(12) United States Patent
Laugharn, Jr.

(10) Patent No.: US 8,409,801 B2
(45) Date of Patent: Apr. 2, 2013

(54) METHOD AND APPARATUS FOR MATERIAL SEPARATION USING ACOUSTIC ENERGY

(75) Inventor: James A. Laugharn, Jr., Winchester, MA (US)

(73) Assignee: Covaris, Inc., Woburn, MA (US)

( * ) Notice: Subject to any disclaimer, the term of this patent is extended or adjusted under 35 U.S.C. 154(b) by 420 days.

(21) Appl. No.: 12/698,599

(22) Filed: Feb. 2, 2010

(65) Prior Publication Data

US 2010/0197894 A1 Aug. 5, 2010

Related U.S. Application Data

(60) Provisional application No. 61/149,788, filed on Feb. 4, 2009.

(51) Int. Cl.
*C12Q 1/68* (2006.01)

(52) U.S. Cl. .......................................... 435/6.1

(58) Field of Classification Search .................. None
See application file for complete search history.

(56) References Cited

U.S. PATENT DOCUMENTS

| | | | |
|---|---|---|---|
| 5,648,124 A | 7/1997 | Sutor | |
| 6,284,470 B1 * | 9/2001 | Bitner et al. | 435/6.16 |
| 6,617,105 B1 * | 9/2003 | Rudi et al. | 435/6.11 |
| 6,682,940 B2 | 1/2004 | Pankowsky | |
| 6,948,843 B2 | 9/2005 | Laugharn, Jr. et al. | |
| 7,090,774 B1 | 8/2006 | Holman | |
| 2006/0264620 A1 | 11/2006 | Lee et al. | |
| 2008/0124777 A1 * | 5/2008 | Stone | 435/173.1 |

FOREIGN PATENT DOCUMENTS

WO WO 2007/ 136 717 A1 11/2007

OTHER PUBLICATIONS

Beckman Coulter Genomics, *Products*, http://www.beckmangenomics.com/products.html © 2010 (2 pages).
Thermo Scientific, *Particle Technology*, http://www.thermo.com/com/cda/landingpage/0,10255,1864.00.html © 2009 (1 page).
Thermo Scientific, *General Purpose Microparticles Microparticles*, http://www.thermo.com/com/cda/landingpage/0,10255,1866,00.html © 2009 (1 page).

\* cited by examiner

*Primary Examiner* — Christopher M. Babic
(74) *Attorney, Agent, or Firm* — Wolf, Greenfield & Sacks, P.C.

(57) ABSTRACT

A method and apparatus for exposing a sample, including a liquid and another material, to sonic energy to produce a desired result such as, suspending a material support in the liquid. The material support may be a bead or other particle with at least one surface feature to which the material may bind. Material in the liquid may attach to the material support, such as by specific or non-specific binding, entrapment or other, so as to facilitate separation of the material from the liquid. Separation of the material supports from the liquid and other unbound material may be done by allowing the material supports to settle out, e.g., under the force of gravity and/or as assisted by centrifugation, by applying a magnetic field in case the supports or material bound to the supports are movable by way of a magnetic field, or other techniques.

21 Claims, 2 Drawing Sheets

METHOD AND APPARATUS FOR MATERIAL SEPARATION USING ACOUSTIC ENERGY

This invention relates to separating materials, such as genetic compounds from a liquid.

SUMMARY OF INVENTION

Aspects of the invention relate to apparatus and methods for exposing a sample, including a liquid and another material, to sonic energy to produce a desired result such as, suspending a material support in the liquid. The material support may be a bead or other particle with at least one surface feature to which the material may bind. Thus, material in the liquid may bind to the material support (whether specifically or non-specifically), or may be entrapped by the material support, so as to separate the material from the liquid. In one example, the material support may include a plurality of polymer beads that are arranged to bind with a selected type of DNA fragment (a material) in a liquid. By binding DNA fragments to the polymer beads, the fragments may be separated from the liquid, and/or from other fragments or material in the liquid. Separation of the material supports from the liquid and other unbound material may be done by allowing the material supports to settle out, e.g., under the force of gravity and/or as assisted by centrifugation, by applying a magnetic field in case the supports or material bound to the supports are movable by way of a magnetic field, or other techniques.

As mentioned above, acoustic energy applied to a sample may be suitable to suspend and/or declump material supports in the liquid, e.g., by causing movement of the liquid that causes the material supports to move and generally be suspended away from walls of a vessel in which the liquid is contained. The acoustic energy may also be suitable, or be adjusted, to cause other effects in the liquid, such as heating the sample, cooling the sample, fluidizing the sample, mixing the sample, stirring the sample, catalyzing the sample, disrupting the sample (such as shearing or fragmenting DNA molecules or other compounds, lysing cells, etc.), permeabilizing a component of the sample, enhancing a reaction in the sample (such as binding of material to the material supports), causing flow in a conduit, and/or sterilizing the sample. Thus, the acoustic energy may be used for other purposes than merely suspending material supports in the liquid. For example, the acoustic energy may facilitate chemical or other reactions in the liquid, which generate an end product (material) that is to be separated from the liquid and other substances in the liquid. The acoustic energy may facilitate the chemical reaction(s) as well as suspend the material supports such that after the end product is created, at least some of the end product will bind with a material support (and allow later separation of the material support and bound end product from the liquid.) For example, by declumping the material supports, the surface area of the active or binding sites on the material support may be increased, thereby accelerating the desired process. In addition, under the applied acoustic energy, a controlled active turbulent regime may exist, whereby the collision frequency between binding partners is increased. This actively controlled turbulence may accelerate desired processes, as opposed to passive diffusion dominated processes of paramagnetic or other currently available bead products.

In one aspect of the invention, a method for separating one or more types of materials from a liquid includes providing a vessel containing a sample including a liquid and a material in the liquid, and providing a material support in the sample having a binding feature arranged to attach at least some of the material to the material support. The material may attach to the material support by specific or non-specific binding, entrapment, or other mechanisms, and the material support may have a density that is greater than the liquid. The sample may be subjected to a focal zone of acoustic energy suitable to cause mixing and/or cavitation in the sample such that the material support is suspended in the liquid, and material may be attached to the material support while the material support is suspended in the liquid. After termination or reduction of the acoustic energy, the material support and the attached material may be separated from the liquid. In one embodiment, the material supports may settle out of the liquid, e.g., within 2 seconds or less, allowing for relatively rapid separation without requiring other tools, such as magnetic field generating devices.

The samples can be treated in any convenient vessel or container. Vessels can be sealed for the duration of the treatment to prevent contamination of the sample or of an environment outside of the vessel. Arrays of vessels can be used for processing large numbers of samples. These arrays can be arranged in one or more high throughput configurations. Examples include microtiter plates, typically with a temporary sealing layer to close the wells, blister packs, similar to those used to package pharmaceuticals such as pills and capsules, and arrays of polymeric bubbles, similar to bubble wrap, preferably with a similar spacing to typical microtiter wells. Vessels containing the samples can be sealed during the processing, and hence can be sterile throughout, or after, the procedure. Moreover, the use of focused ultrasound allows the samples in the vessels to be processed, including processing by stirring, without contacting the samples, even when the vessels are not sealed. The sample container can be a membrane pouch, thermopolymer well, polymeric pouch, hydrophobic membrane, microtiter plate, microtiter well, test tube, centrifuge tube, microfuge tube, ampoule, capsule, bottle, beaker, flask, and/or capillary tube.

The material can include a polymer, an amino acid monomer, an amino acid chain, a protein, an enzyme, a nucleic acid monomer, a nucleic acid chain, a saccharide, a polysaccharide, a lipid, an organic molecule, an inorganic molecule, a vector, a plasmid, a prion, a bacteria, and/or a virus.

These and other aspects of the invention will be apparent from the following description and claims.

BRIEF DESCRIPTION OF THE DRAWINGS

Aspects of the invention are shown and described with reference to illustrative embodiments and the following drawings, in which like numerals reference like elements, and wherein.

DETAILED DESCRIPTION

Figure 1:
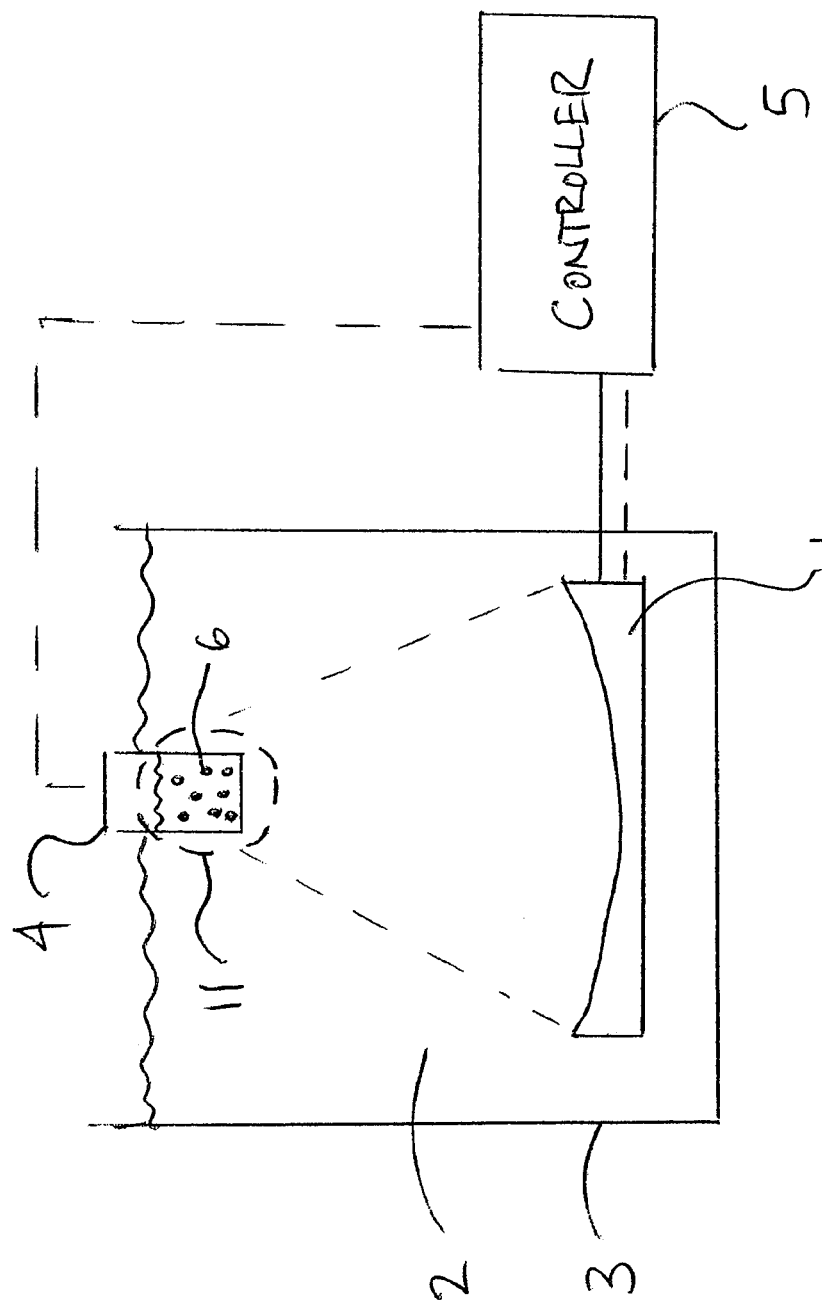
FIG. 1 shows a schematic diagram of an acoustic treatment system in accordance with an aspect of the invention.

FIG. 1 shows a schematic diagram of an acoustic treatment system 100 that incorporates one or more aspects of the invention. In this illustrative embodiment, the system 100 includes an acoustic transducer 1 that is arranged to emit sonic energy through a couplant medium 2 (such as water held in a container 3 or a solid material in contact with the transducer 1) and form a focal zone 11 of acoustic energy near or at a vessel 4. The acoustic energy at the focal zone may be suitable to cause mixing, cavitation or other effects in a sample located in the vessel 4. A controller 5 may provide suitable control signals to the transducer 1 to generate desired acoustic energy, and control the relative position of the vessel 4 and the transducer 1 (e.g., in 3 dimensions) so that the sample in the vessel 4 may be suitably positioned relative to the focal zone 11. Further details regarding an illustrative embodiment for an acoustic treatment system 100 are provided below, and in U.S. Pat. No. 6,948,843, which is incorporated herein by reference in its entirety.

In accordance with an aspect of the invention, the sample in the vessel 4 may include one or more material supports 6 (also referred to herein as beads, though not limited to a spherical shape) that are located in a sample including a liquid and a material in the liquid. The material may be any suitable compound, such as DNA or other genetic material, antibodies, receptors and/or ligands associated with cellular functions, proteins, and others. The material supports 6 may be arranged to bind with the material (e.g., by way of a chemical bond) such that the material is attached to the material support 6 to allow the material support 6 and attached material to be separated from the liquid and other substances in the sample. Bead separation techniques are widely known in the art, and often employ the use of magnetic beads and a magnetic field to separate beads and attached material from a sample.

In accordance with one aspect of the invention, the material supports 6 may be arranged to allow suspension of the beads 6 in the sample liquid when suitable acoustic energy is applied at the focal zone 11. This acoustic energy may also be suitable to cause mixing of the sample, cavitation in the sample, heating in the sample, disruption in the sample (e.g., DNA molecules may be sheared by the acoustic energy into smaller DNA fragments), catalyzing of reactions in the sample (e.g., catalyzing binding of material to material supports 6), and others. Suspension of the beads 6 may permit the material to more readily contact and bind with the beads, potentially enhancing the rate at which material binds to the beads 6. Thus, the acoustic energy may be suitable to overcome the force of gravity (which may tend to pull the beads 6 toward the bottom of the vessel 4), or other force that tends to cause the beads 6 either to clump together in bunches of two or more, or to otherwise collect in one or more areas of the vessel. For example, the beads 6 may be magnetic such that the beads 6 tend to attach to each other (e.g., clump together) in the absence of a force that separates the beads 6. In another aspect of the invention, the beads 6 may be hydrophobic so that when the beads 6 are in a liquid containing water, the beads 6 will tend to clump together. In accordance with an aspect of the invention, acoustic energy at the focal zone 11 may cause mixing or other disturbance in the sample so that the beads 6 tend to be suspended and "declumped" or separated from other beads 6, even if the beads 6 are magnetic, hydrophobic or otherwise arranged to clump together.

In accordance with another aspect of the invention, the material supports may be arranged so as to separate from the liquid and other material in the sample (e.g., settle to the bottom of the vessel under the force of gravity). For example, the material supports may be arranged to have a density relative to the liquid such that a substantial majority (e.g., greater than 60%, greater than 70%, greater than 80%, greater than 90%, greater than 95%, or greater than 99%) of the material supports settle to a bottom of the vessel under the force of gravity in an absence of the acoustic energy. In one embodiment, beads 6 may have a density that is approximately 1% or more of the liquid in the vessel. In a specific embodiment, in a 100 μl liquid in a vessel whereby the liquid/air interface is 1 cm from the bottom of the vessel, a suitable portion of the material supports may settle to the bottom within less than about 2 seconds after the liquid is no longer subjected to acoustic energy. The rate of settling is proportional to the aspect ratio of the vessel and the volume; a tall, narrow column of liquid will generally take longer to settle than a short, wide basin of liquid. Thus, in one embodiment, beads 6 and their attached material may be separated from a sample without the use of an external magnetic field, centrifugation or other techniques. Instead, the beads may be permitted to settle out in a vessel 4, and the liquid and/or other materials decanted, aspirated or otherwise removed from the vessel 4.

Figure 2:
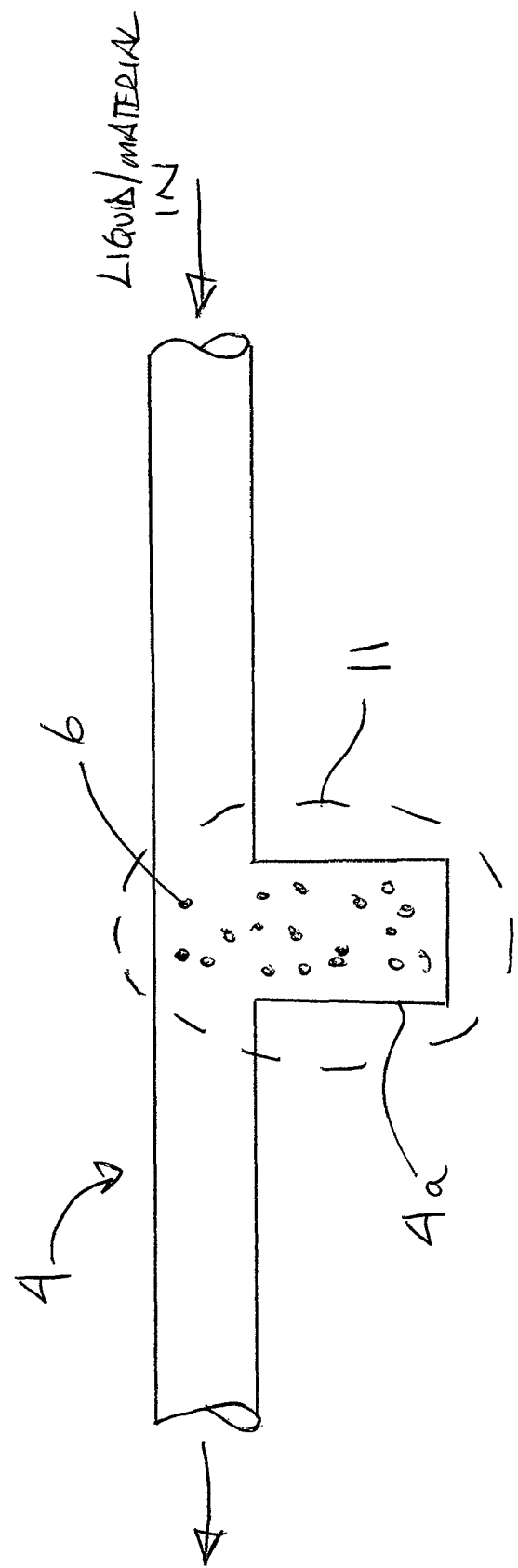
FIG. 2 shows a schematic diagram of a vessel in a illustrative embodiment.

FIG. 2 shows another illustrative embodiment that incorporates aspects of the invention. In this embodiment, the vessel 4 has an arrangement that allows for the flow through of a sample (e.g., including liquid and a material to be bound to beads 6). Beads 6 may be located at a well 4a or other feature of the vessel 4 and arranged so that when subjected to suitable acoustic energy at the focal zone 11, the beads 6 may be suspended at least in part in a region where the sample is flowing through the vessel 4. Thus, beads 6 may be positioned in an approximately stationary way relative to sample liquid that flows past the beads 6. Material in the sample liquid may bind to the beads 6, and the beads 6 may be circulated generally in the well 4a area so that material is separated from the liquid and bound to the beads 6. After suitable treatment, the acoustic energy may be stopped, and the beads 6 may collect in the well 4a. The well 4a may be removed and the beads 6 and material recovered or otherwise used. It should be appreciated that the vessel 4 may include a screen, magnetic field or other arrangement to help prevent beads 6 from flowing with the sample, if required. Alternately, the beads 6 may be "ejected" or otherwise introduced into the flow stream of the sample in the vessel and allowed to travel downstream of the well 4a for collection at another point.

The beads 6 in accordance with aspects of the invention may have any suitable configuration, e.g., may be made of glass, a polymer material, a magnetic material, a metal, a ceramic, or any suitable combination of materials. For example, a bead may have a polymer core, with a magnetite or other magnetic material layer over the core, and a polymer layer over the magnetic layer. Beads may have any suitable components to facilitate specific binding of material to the bead, such as genetic fragments (e.g., primers or other), antigen receptors, or other arrangements. A bead may be arranged to bind with a single piece of material, e.g., a single protein molecule, or may bind with multiple pieces of material. Suitable bead materials may be prescreened in an appropriate liquid to remove lower density and/or slower settling subpopulations from the bulk material. Beads may also have interstitial spaces with appropriate charge density and/or hydrophobic domains to non-specifically interact with a material in the liquid.

The controller 5 may be arranged to control the transducer 1 in any suitable way, e.g., generate a variety of alternating voltage waveforms to drive the transducer 1. For instance, a high power "treatment" interval consisting of about 5 to 1,000 sine waves, for example, at 1.1 MHz, may be followed by a low power "convection mixing" interval consisting of about 1,000 to 1,000,000 sine waves, for example, at the same frequency. "Dead times" or quiescent intervals of about 100 microseconds to 100 milliseconds, for example, may be programmed to occur between the treatment and convection mixing intervals. Also, the focal zone 11 may be arranged in any suitable way, e.g., may be small relative to the dimensions of the vessel 4 to avoid heating of the treatment vessel, or may be larger than the vessel 4. In one embodiment, the focal zone 11 may have a width of about 2 cm or less, a height of about 6 cm or less and a length of 5 cm or more. In another embodiment, the focal zone 11 may have an ellipsoidal shape, with a width or diameter of about 2 cm or less and a length of about 6 cm or less. Acoustic energy in the focal zone 11 may generate a shock wave that is characterized by a rapid shock front with a positive peak pressure in the range of about 15 MPa, and a negative peak pressure in the range of about negative 5 MPa. This waveform may be of about a few microseconds duration, such as about 5 microseconds. If the negative peak is greater than about 1 MPa, cavitation bubbles may form in liquid in the sample. Cavitation bubble formation also may also be dependent upon the surrounding medium 2, the vessel material, or other features. For example, glycerol is a cavitation inhibitive medium, whereas liquid water is a cavitation promotive medium. The collapse of cavitation bubbles may form "microjets" and turbulence that impinge on the surrounding material. These cavitation bubbles may contribute to suspension of beads 6 during a treatment.

In the embodiments shown, the acoustic energy is transmitted from the transducer 1 to the vessel 4 through a medium 2, such as water. However, other media or combinations of media may be used, such as a solid or semi-solid material and others.

Many biological and other materials can be treated according to aspects of the invention. For example, such materials for treatment include, without limitation, growing plant tissue such as root tips, meristem, and callus, bone, yeast and other microorganisms with tough cell walls; bacterial cells and/or cultures on agar plates or in growth media, stem or blood cells, hybridomas and other cells from immortalized cell lines, and embryos. Additionally, other biological materials, such as serum and protein preparations, can be treated with the processes of the invention, including sterilization. For example, the extraction of RNA from a piece of muscle tissue (5 mg) that had been chemically stabilized against RNase digestion may be placed into a 6×16 mm annealed, borosilicate, round bottom glass test tube with 50 mg of 0.1 mm borosilicate glass beads. A snap-cap with a pre-split Teflon/silicone septa is placed on the tube to seal the sample. A 100 μl volume of a RLT extraction buffer (Qiagen, Hilden, Germany) is introduced to the sample through the septa. The applied acoustic energy disrupts the tissue sample and is accelerated by the presence of the glass beads. Upon termination of the acoustic dose, the beads settle to the bottom of the tube and entrap remaining particulate material. The top portion of the remaining homogenate (approximately 50 μl) is readily aliquoted. Alternatively, the tissue sample may be disrupted with 100 μl distilled water. This would enable beads to non-specifically bind with nucleic acids. In this format, the resultant homogenate may be removed, the beads resuspended in a low power acoustic dose, and followed by a buffer to release the nucleic acids, such as TrisEDTA, pH 8.0. In this example, the beads at high acoustic power aided disruption, and at low acoustic power aided separation. This two step technique may also be used for formalin cross-linked tissue or cells.

Many binding reactions can be enhanced with treatments according to the invention. Binding reactions involve binding together two or more molecules, for example, two nucleic acid molecules, by hybridization or other non-covalent binding. Binding reactions are found, for example, in an assay to detect binding, such as a specific staining reaction, in a reaction such as the polymerase chain reaction where one nucleotide molecule is a primer and the other is a substrate molecule to be replicated, or in a binding interaction involving an antibody and the molecule it binds, such as an immunoassay. Reactions also can involve binding of a substrate and a ligand. For example, a substrate such as an antibody or receptor can be immobilized on a support surface, for use in purification or separation techniques of epitopes, ligands, and other molecules.

In certain embodiments, temperature, mixing, or both can be controlled with ultrasonic energy to enhance a chemical reaction. For example, the association rate between a ligand present in a sample to be treated and a binding partner on a bead 6 can be accelerated. In another example, an assay is performed where temperature is maintained and mixing is increased to improve association of two or more molecules compared to ambient conditions. It is possible to combine the various aspects of the process described herein by first subjecting a mixture to heat and mixing in order to separate a ligand or analyte in the mixture from endogenous binding partners in the mixture. The temperature, mixing, or both, are changed from the initial condition to enhance ligand complex formation with a binding partner relative to ligand/endogenous binding partner complex formation at ambient temperature and mixing. Generally, the second temperature and/or mixing conditions are intermediate between ambient conditions and the conditions used in the first separating step above. At the second temperature and mixing condition, the separated ligand may be reacted with the binding partner.

Focused sonic fields can be used to enhance separations. As noted elsewhere, sonic foci can be used to diminish or eliminate wall effects in fluid flow, which is an important element of many separation processes, such as chromatography including gas chromatography, size exclusion chromatography, ion exchange chromatography, and other known forms, including filed-flow fractionation. The ability to remotely modulate and/or reduce or eliminate the velocity and concentration gradients of a flowing stream is applicable in a wide variety of situations, such as those described in relation to FIG. 2.

Sonic energy fields can be used to enhance reaction rates in a viscous medium, by providing remote stirring on a micro scale with minimal heating and/or sample damage. For example, some assays rely on the absorption of analytes by reagents, such as antibodies, which are bound to macroscopic beads 6. In a viscous fluid to be analyzed, such as sputum or homogenized stool, the ability to stir such a sample remotely, aseptically, and essentially isothermally can significantly decrease the time required to obtain equilibrium of the analyte with the reagents on the particle.

Likewise, any bimolecular (second-order) reaction where the reactants are not mixed at a molecular scale, each homogenously dissolved in the same phase, potentially can be accelerated by sonic stirring. At scales larger than a few nanometers, convection or stirring can potentially minimize local concentration gradients and thereby increase the rate of reaction. This effect can be important when both reactants are macromolecules, such as an antibody and a large target for the antibody, such as a cell, since their diffusion rates are relatively slow and desorption rates may not be significant.

These advantages may be realized inexpensively on multiple samples in an array, such as a microtiter plate. The use of remote sonic mixing provides a substantially instantaneous start time to a reaction when the sample and analytical reagents are of different densities, because in small vessels, such as the wells of a 96 or 384 well plate, little mixing will occur when a normal-density sample (about 1 g/cc) is layered over a higher-density reagent mixture. Remote sonic mixing can start the reaction at a defined time and control its rate, when required. Stepping and dithering functions may allow multiple readings of the progress of the reaction to be made. The mode of detecting reaction conditions can be varied between samples if necessary. In fact, observations by multiple monitoring techniques, such as the use of differing optical techniques, can be used on the same sample at each pass through one or more detection regions.

By focusing sonic energy and positioning it near a wall of a vessel, a wall of a tube, or another discontinuity in a fluid path, many local differences in the distribution of materials within a sample and/or spatially-derived reaction barriers, particularly in reactive and flowing systems, can be reduced to the minimum delays required for microscopic diffusion. Put differently, enhanced mixing can be obtained in situations where imperfect mixing is common. For example, if sonic energy is focused in, on, or near the wall of the pipe, near the fluid/wall boundary, then local turbulence can be obtained without a high rate of bulk fluid flow. Excitation of the near-wall fluid in a continuous, scanned, or burst mode can lead to rapid homogenization of the fluid composition just downstream of the excited zone. This will sharpen the front between any two fluids passing through a pipe in succession.

This effect is useful in several areas, including chromatography; fluid flow in analytical devices, such as clinical chemistry analyzers; and conversion of the fluid in a pipeline from one grade or type to another. Since most of the effect occurs in a narrow zone, only a narrow zone of the conduit typically needs to be sonically excited. For example, in some applications, the focal zone of the sonic energy can be the region closest to a valve or other device which initiates the switch of composition. In any of these applications, feedback control can be based on local temperature rise in the fluid at a point near to or downstream of the excitation region.

While there has been described herein what are considered to be exemplary and preferred embodiments of the invention, other modifications and alternatives of the inventions will be apparent to those skilled in the art from the teachings herein. All such modifications and alternatives are considered to be within the scope of the invention.

The invention claimed is:

1. A method for separating one or more types of materials from a liquid, comprising:
   providing a vessel containing a sample including a liquid and a material in the liquid;
   providing a material support having a binding feature arranged to attach at least some of the material to the material support, the material support being provided in the vessel and having a density that is greater than the liquid;
   subjecting the sample and the material support to a focal zone of acoustic energy so as to cause mixing and/or cavitation in the sample and attachment of the material of the sample to the material support; and
   separating the material support and the attached material from the liquid after termination or reduction of acoustic energy.

2. The method of claim 1, wherein the material support includes a bead that is magnetic or non-magnetic.

3. The method of claim 1, wherein the material is a genetic material, a DNA or RNA fragment, a molecule, a protein, an antibody, or a drug.

4. The method of claim 1, wherein the binding feature includes a substance arranged to chemically bind, specifically or non-specifically, with the material.

5. The method of claim 1, wherein the step of separating includes:
   allowing the material support and attached material to move in the liquid under the force of gravity.

6. The method of claim 5, wherein the material support and attached material settle to a bottom of the vessel.

7. The method of claim 1, wherein the acoustic energy in the focal zone is suitable to shear or otherwise break portions of the material into smaller pieces.

8. The method of claim 7, wherein the material includes pieces of DNA or other genetic material that is sheared into smaller fragments by the acoustic energy.

9. The method of claim 8, wherein the step of attaching includes binding one or more fragments of DNA or other genetic material to the material support.

10. The method of claim 1, wherein the step of providing a material support includes providing a plurality of material supports, each separate from other material supports.

11. The method of claim 1, wherein the step of attaching includes:
    using acoustic energy to facilitate binding of material to the material support.

12. The method of claim 1, wherein the density of the material support is approximately 1% or greater than a density of the liquid.

13. The method of claim 1, wherein the material support includes a plurality of beads made from a polymer, glass or ceramic material.

14. The method of claim 1, wherein the material support includes a plurality of material supports with a density relative to the liquid such that a substantial majority of the material supports settle to a bottom of the vessel under the force of gravity in an absence of the acoustic energy.

15. The method of claim 14, wherein the substantial majority of the material supports settle to the bottom within less than about 2 seconds after the liquid is no longer subjected to the acoustic energy.

16. The method of claim 1, wherein the material supports include a hydrophobic surface feature that causes material supports to clump together in the presence of water.

17. The method of claim 16, wherein the acoustic energy in the focal zone has a sufficient energy to declump and separate material supports from each other.

18. The method of claim 1, wherein the vessel includes a flow stream in which the liquid and material flow, and wherein the material support is suspended in a stationary fashion relative to the flow stream such that the liquid and material flow past the material support.

19. The method of claim 18, wherein the material support is suspended in a portion of the flow stream having generally turbulent flow.

20. The method of claim 1, wherein the vessel is a tube-shaped container that is closed at a top opening by a lid.

21. The method of claim 1, wherein subjecting the sample and the material support to a focal zone of acoustic energy causes the material support to be suspended in the liquid.

* * * * *